United States Patent [19]

Bahl et al.

[11] Patent Number: 5,324,829
[45] Date of Patent: Jun. 28, 1994

[54] HIGH SPECIFIC ACTIVITY NUCLEIC ACID PROBES HAVING TARGET RECOGNITION AND SIGNAL GENERATING MOIETIES

[75] Inventors: Chander Bahl, Flemington, N.J.; Leopoldo Mendoza, Madison, Wis.

[73] Assignee: Ortho Diagnostic Systems, Inc., Raritan, N.J.

[21] Appl. No.: 285,274

[22] Filed: Dec. 16, 1988

[51] Int. Cl.$^5$ .................. C16Q 1/68; G01N 33/53; C07H 21/04; C12Q 1/68
[52] U.S. Cl. ........................... 536/23.1; 435/6; 536/22.1; 536/24.2; 536/25.3; 536/25.4; 935/17; 935/77; 935/78
[58] Field of Search .............. 435/6, 91; 536/27, 22.1, 536/23.1, 25.3, 24.2, 25.4; 935/17, 77, 78

[56] References Cited

U.S. PATENT DOCUMENTS

| | | | |
|---|---|---|---|
| 4,358,535 | 11/1982 | Falkow et al. | 435/5 |
| 4,458,066 | 7/1984 | Caruthers et al. | 536/27 |
| 4,486,539 | 12/1984 | Ranki et al. | 436/504 |
| 4,533,628 | 8/1985 | Maas | 435/6 |
| 4,556,643 | 12/1985 | Paau et al. | 436/501 |
| 4,563,419 | 1/1986 | Ranki et al. | 435/6 |
| 4,623,618 | 11/1986 | Rokugawa | 435/6 |
| 4,711,955 | 12/1987 | Ward et al. | 536/29 |
| 4,717,653 | 1/1988 | Webster | 435/5 |
| 4,794,082 | 12/1988 | Sigler et al. | 435/177 |
| 4,816,389 | 3/1989 | Sansonetti et al. | 435/6 |
| 4,851,331 | 7/1989 | Vary et al. | 435/6 |

FOREIGN PATENT DOCUMENTS

| | | |
|---|---|---|
| 0079139 | 5/1983 | European Pat. Off. . |
| 0097373 | 1/1984 | European Pat. Off. . |
| 0117440 | 9/1984 | European Pat. Off. . |
| 0122614 | 10/1984 | European Pat. Off. . |
| 0123300 | 10/1984 | European Pat. Off. . |
| 0154788 | 1/1985 | European Pat. Off. . |
| 0194545 | 9/1986 | European Pat. Off. . |
| 0212546 | 3/1987 | European Pat. Off. . |
| 0219695 | 4/1987 | European Pat. Off. . |
| 0221308 | 5/1987 | European Pat. Off. . |
| 0224126 | 6/1987 | European Pat. Off. . |
| 0231495 | 8/1987 | European Pat. Off. . |
| 0235726 | 9/1987 | European Pat. Off. . |
| 0237737 | 9/1987 | European Pat. Off. . |
| 0285057 | 10/1988 | European Pat. Off. . |
| 0286898 | 10/1988 | European Pat. Off. . |
| 0292128 | 11/1988 | European Pat. Off. . |
| WO83/01459 | 4/1983 | PCT Int'l Appl. . |
| WO84/03285 | 8/1984 | PCT Int'l Appl. . |
| WO85/04674 | 10/1985 | PCT Int'l Appl. . |
| WO97/03911 | 7/1987 | PCT Int'l Appl. . |
| WO88/01302 | 2/1988 | PCT Int'l Appl. . |
| 87/03622 | 6/1987 | World Int. Prop. O. . |

OTHER PUBLICATIONS

Ghosh et al. (1987) Nucleic Acids Research, vol. 15, No. 13, pp. 5353–5372.
Chu et al. (1988) Nucleic Acids Research, vol. 16, No. 9, pp. 3671–3691.

(List continued on next page.)

Primary Examiner—Margaret Parr
Assistant Examiner—Ardin H. Marschel
Attorney, Agent, or Firm—Woodcock Washburn Kurtz Mackiewicz & Norris

[57] ABSTRACT

The probes of the invention are made up of a target recognition moiety and a signal generation moiety. In the first step of the preparatory method of the invention, the 5' or 3' terminus or both of the target recognition moiety is chemically altered to incorporate a reactive functionality which will allow chemical linkage of this target recognition moiety with one or both termini of the signal generation moiety of the probe. Suitable functionalities vary widely, but may, in general be described as those that allow chemical attachment of the two moieties either at the 5' or 3' end of the target recognition moiety. The two moieties should not detach from each other upon hybridization of the target moiety to the target analyte. Thus, when the probe is hybridized to target analyte, it will then carry with it, signal moiety, to label this complex, which label is then later detected.

4 Claims, 2 Drawing Sheets

OTHER PUBLICATIONS

Stavriamopoulos et al. (1985) Federation Proceedings, vol. 44, No. 5, p. 1622.

Bauman, J. (1985) Acta Histochemica, Suppl.-Band XXXI, pp. 9–18.

Sigma Chemical Catalog, p. 771 (St. Louis, MO) 1987 edition.

T. Brown et al., "Modern Machine—aided Methods of Oligodeoxyribonucleotide Synthesis", in *Oligonucleotides and Analogues—A Practical Approach,* F. Eckstein, Editor Oxford University Press, New York, N.Y., 1991, pp. 1–24.

Van der Ploeg, M., Folia Histochemica et Cytobiologica 24:189–194 (1986).

Sodja, A. et al., Nucleic Acids Research 5:385–401 (1978).

Manning et al., Chromosoma 53:107–117 (1975).

Broker, et al., Nucleic Acids Research 5:363–384 (1978).

Manning, et al., Biochemistry 16:1364–1370 (1977).

Langer, et al., Proc. Natl. Acad. Sci., USA 78:6633–6637 (1981).

Clegg & Gerlach, J. Bacteriology 169:934–938 (1987).

Moseley, et al., J. Infectious Diseases 142:892–898 (1980).

Amarnath & Broom, Chemical Reviews 77:183–217 (1977).

HIGH SPECIFIC ACTIVITY NUCLEIC ACID PROBES HAVING TARGET RECOGNITION AND SIGNAL GENERATING MOIETIES

BACKGROUND OF THE INVENTION

Specific oligonucleotide sequences are very useful tools in detecting complementary nucleotide sequences. The two requirements of the nucleic acid probe are a sequence specific signal and the formation of elements which will convert single hybridization events into multiple detectable events. In current enzymatic methods for preparing labeled probes, radioactive or biotinylated nucleotides are introduced into the probes by the use of polymerizing enzymes like DNA polymerase or terminal transferase. Methods are also available for introducing single enzymes or hapten molecules into DNA chemically, but these singly tagged probes do not generate enough signal, thus lacking the sensitivity needed for detecting complementary sequences in biological samples.

For example, Ward et al. in U.S. Pat. No. 4,711,955, discloses a procedure for derivatizing nucleotides with chemical determinants. The derivatized nucleotides are then enzymatically polymerized. Thus, these analogs function as substrates for nucleic acid polymerases. For this purpose, it is crucial that the chemical determinants not be placed on ring positions that sterically, or otherwise, interfere with normal Watson Crick hydrogen bonding potential of the bases.

SUMMARY OF THE INVENTION

The present invention provides an alternative to the syntheses of labeled nucleic acid probes known to the art. The procedure disclosed herein is a chemical synthesis of a labeled "nucleotide probe" which comprises the steps of:

a) providing a first "target recognition moiety" comprising a nucleotide sequence of at least about 10 nucleotide bases, said sequence containing at least one "5' end" and "3' end", b) chemically altering said first target recognition moiety to contain a "reactive functionality" at said 5' end or said 3' end, or both, and c) providing a second "signal generating moiety", having at least one terminus containing a functionality capable of reacting with at least one reactive functionality provided on said first target recognition moiety, and d) chemically reacting said first target recognition moiety, now containing at least one reactive functionality, with said at least one terminus of said second signal generating moiety, to chemically join these two moieties and produce said labeled nucleotide probe.

In some embodiments, one or both termini of the signal generating moiety are chemically modified to contain a functionality that will react with one or both of the reactive functionalities of the target recognition moiety.

The present invention also provides labeled nucleotide probes formed from this chemical joinder of the two components, and diagnostic and research reagents containing said probes.

As used herein, the term "nucleotide probe" means a labeled nucleotide sequence having as part of that sequence, a moiety that can hybridize, at least in part, to an analyte nucleotide sequence, and can be useful to detect, monitor, localize, isolate and the like, said analyte sequence. The term should be interpreted broadly to include oligonucleotides, homopolynucleotides, polynucleotides and the like.

As used herein, it is understood that "hybridization" refers to complementary base pair binding to all or a portion of a target nucleic acid sequence, i.e.: the probes must contain at least some complementarity. It should be understood that this binding does not have to be perfectly matched. There may, in fact, be unpaired regions, resulting in interior loops, bulge loops, hairpin loops, cruciform binding, or any other mismatched regions. Hybridization need only occur to the extent necessary to allow detection of the target.

As used herein, the term "target recognition moiety" (TRM) means that part of the probe that will hybridize or bind to sample analyte. The target recognition moiety comprises a nucleotide sequence and can take on any suitable configuration for binding to said analyte, whether that be a specific sequence of nucleotide bases, a homopolynucleotide sequence, or the like.

As used herein, "signal generating moiety" (SGM) means that part of the probe that can generate a signal through a radioactive label, enzymatic label, chemical label, immunogenic label, and the like.

As used herein, "target analyte sequence" refers to all or a portion of the nucleic acid contained in or relating to biological matter that may be found in a biological, physiological, environmental sample or the like.

As used herein, "5' end" and "3' end" should be construed as the meaning generally accepted in the art, namely, the terminal nucleotide at one end of a nucleotide sequence which has a free 5' or 3' group, wherein one of the oxygens of the phosphorus is free to join to either the fifth or third carbon atom respectively of a pentose.

Chemical synthesis of the probes as described herein provides advantages in that a more controlled amount of label is incorporated into the signal generating moiety. Thus, amplification of signal may be easily accomplished. The label may be applied to various positions on the signal generating moiety, when that moiety is a polynucleotide. In preferred embodiments, the signal-generating moiety is a polynucleotide and the label is applied to positions on the polynucleotide that will interfere with the capability of this nucleotide to hybridize, thus ensuring that only the target recognition moiety hybridizes to target analyte. Not only does the signal generating moiety not have to be available for nucleic acid hybridization, in some embodiments, the signal generating moiety may even comprise polymers other than polynucleotides, and therefore couldn't be available to hybridize.

DETAILED DESCRIPTION OF THE INVENTION

The present invention provides a procedure for chemical synthesis of a labeled nucleotide probe by a chemical coupling or joinder of the two components of the probe, namely the target recognition sequence moiety and the signal generating moiety.

The first component of the labeled nucleotide probes of the invention is the target recognition sequence moiety, which comprises a nucleotide sequence of at least about 10 nucleotide bases. This moiety is capable of hybridizing in whole or in part to target analyte. It may be provided in any of a variety of ways. For example, it may be isolated from the genomic DNA of an organism it is desired to detect, it may be recombinantly produced, or it may be chemically synthesized by standard oligonucleotide synthesis procedures. A good description of such suitable procedures for the latter may be found in Methods in Enzymology, Volume 154, pages 221-328, Academic Press N.J. 1987, Ray Wu and L. Grossman, editors. Any configuration of nitrogenous bases, including adenine, guanine, cytosine, thymine, uracil, or methylcytosine, are contemplated to form the nucleotide sequence of this moiety, as long as the moiety is capable of binding, at least to some extent, with at least a portion of the nucleic acid of an analyte.

The binding event is any complementary base pair binding to an extent suitable to allow detection of the target analyte. In this regard then, the length of the nucleotide sequence of the target recognition moiety may also vary widely, ranging from several hundred bases to less than about 100 bases, and preferably about 5-75, more preferably about 5-60, and most preferably about 15-50 bases. At this time, these latter sequence lengths are preferred in that it has been found that this length affords ease of use. This is generally due to the phenomenon that sequences in the range of 15 to 50 nucleotide bases are easy to synthesize conveniently, and cost effectively, and have enough hydrogen bonding capability to give stable double-stranded structure to survive various manipulations and treatments. Sequences of greater than about 100 bases can pose difficulty during use in that they are more difficult to synthesize, less cost effective and increase the chances of fostering intramolecular secondary structures. It is well known that beyond a certain length of polynucleotide sequence, very little additional stability would be imparted to the hybrids. One skilled in the art will appreciate that a suitable sequence length for this binding moiety will also be governed to some extent by the binding characteristics of the analyte sequence itself.

It should be appreciated that in some instances it may be desirable to incorporate derivatives or other chemical moieties at various positions in the nucleotide sequence of the target recognition moiety, for a variety of reasons such as to serve as reporter molecules directly or indirectly. For example, derivatives such as 5 substituted pyrimidine and 7 substituted purine may be desired. Any such derivatives are within the contemplation of the invention, as long as the addition of such chemical derivatives to various positions in the sequence does not interfere substantially with binding of target recognition moiety to analyte.

The second component of the probes is the signal generating moiety. This comprises any polymer that is capable of containing a detectable label, and is further capable of chemical linkage to the target recognition moiety, by virtue of a functional group on at least one terminus. Illustrative of suitable polymers in this regard are proteins, such as albumin and gelatin, derivatized latex beads, dextrans, other synthetic or natural biopolymers, and nucleotides, including homopolynucleotides, oligonucleotides, and the like. Preferred among these polymers for use in the signal generating moiety, are nucleotide sequences. This may be attributed to their ease of synthesis and labeling, and controllable amplification. These nucleotide sequences may vary widely in their specific sequence, as long as they contain label which is capable of signaling the binding of the target recognition moiety portion of the probe to analyte. The nucleotide sequences may be DNA or RNA. One of the major advantages afforded by the preferred signal generating moiety, the polynucleotide sequence, is the ability for the user to provide multiple labels at defined places in the sequence. This affords more user control then was previously possible. The labeling of the polymer in the signal generating moiety may take on many forms, including conventional radioisotopic labeling, chemical labeling, immunogenic labeling, or a label with light scattering affect, and the like.

Thus, the label of the signal generating moiety may comprise a radiolabel (e.g. $^{14}C$, $^{32}P$ $^{3}H$, and the like), an enzyme (e.g., peroxidase, alkaline or acid phosphatase, and the like), a bacterial label, a fluorescent label, an antibody (which may be used in a double antibody system), an antigen (to be used with a labeled antibody), a small molecule such as a hapten like biotin (to be used with an avidin, streptavidin, or antibiotin system), a hapten such as fluorescein to be used with an antifluorescein, a latex particle (to be used in a buoyancy or latex agglutination system), an electron dense compound such as ferritin (to be used with electron microscopy), or a light scattering particle such as colloidal gold, or any combinations or permutations thereof.

Signal is generated by the signal generating moiety in any variety of conventional techniques. For example, if the label portion of the signal generating moiety is an antigen, a signal can be generated by complexing said antigen with an antibody/enzyme conjugate, followed by addition of enzyme substrate. If the labeling portion of the signal generating moiety is an antibody, signal can be generated by complexing anti-antibody or an $F_c$ binding protein such as Protein A therewith, which second antibody or Protein A has already been conjugated to an enzyme.

For reasons of ease and safety in the handling of the probe, it is preferred that the signal generating moiety be chemically labeled, especially immunogenically or enzymatically. In more preferred embodiments, the chemical label of choice is a hapten, such as biotin, iminobiotin, fluorescein, and the like. These are preferred at the present time due to ease of synthesis, as well as the availability of high specific activity secondary reagents and techniques for using them. For example, the signal generating moiety may be labeled with a hapten through conventional techniques such as treatment with an alkyldiamine. Activated haptens such as biotin-NHS ester, fluorescein isothiocyanate (FITC), and the like may be chemically attached through the amino functionalities. In this manner, the amount of activated hapten present is controlled by the availability of the amino functionalities provided by the user for this purpose, by the treatment with the alkyldiamine.

In one preferred embodiment wherein the signal generating moiety comprises a nucleotide sequence, the signal generating moiety generates signal based on the biotin/streptavidin system. This system can be incorporated into the signal generating moiety by a variety of means. For example, the nucleotide portion of the signal generating moiety can be covalently attached to biotin via a cytochrome c bridge (Manning et al, Biochemistry, 16: 1364–1370 (1977), Manning et al, Chromosoma, 53: 107–117 (1975), Sodja, A., Nucleic Acids Research, 5: 385–401 (1978)), or the biotin can be covalently incorporated into specific nucleotide residues (Langer, P. R., Proceedings of one National Academy of Sciences, USA, 78: 6633–6637 (1981), or, as alluded to above, the biotin can be attached to a polynucleotide by means of a diamine (e.g., pentane diamine) bridge (Broker, T. R. et al, Nucleic Acids Research 5: 363–384 (1978)). Interaction of the biotin molecules in the signal generating moiety with avidin, streptavidin or antibiotin antibodies is then carried out, wherein the avidin, streptavidin or the antibodies are conjugated to such signalling components as latex particles (Sodja, A., et al, supra, or Manning, et al Chromosoma, supra), ferritin (Broker, supra), a fluorogen such as fluorescein, an enzyme, secondary antibodies, magnetic particles, or the like.

It should also be noted that the function of the signal generating moiety is to signal the presence of binding to analyte. Hence, it should be appreciated that it is undesirable for nucleotides within this moiety to hybridize to analyte, or any other bases that may be present in a sample under analysis, as this may quench any signal to be generated. Therefore, it is preferable to substitute the cytosine bases on the fourth carbon atom with a hapten such as biotin, immunobiotin, fluorescein, or the like, to prevent this base's normal hybridization function.

The signal generating moiety may be obtained commercially or prepared from any appropriate source, including denatured single-stranded DNA from natural sources, RNA from material sources, chemical synthesis of oligonucleotides, polynucleotides, including homopolynucleotides and homooligonucleotides. This sequence varies in length in a manner commensurate with the signal amplification required and the amount of label it is desired to attach. However, lengths of about 50 to 200 have been found to be particularly useful due to the amplification required for the detection of biological samples and the practical limitations of synthesizing the long sequence. Also, it should be understood that very long tails will tend to affect hybridization rates. Preferred lengths range from about 50 to about 200, most preferred being about 100 to about 150.

In the first step of the method of the invention, the 5' or 3' terminus or both of the nucleotide sequence of the target recognition moiety is chemically altered to incorporate a reactive functionality which will allow chemical linkage of this target recognition moiety with one or both termini of the second component of the probe, the signal generating moiety. Suitable functionalities vary widely, but may, in general, be described as those that will allow chemical attachment of the two components either at the 3' end or the 5' end of the target sequence. This chemical attachment of the signal generating moiety to the target recognition moiety, forming the probes as described herein, is robust to disassociation of these two moieties in the subsequent use of the probes in hybridization assays. In other words, the two components of the probe should not detach from each other upon hybridization of the target sequence moiety of the probe to target analyte. Thus, when the probe is hybridized to target analyte, it will then carry with it, signal moiety, to label this complexation, which label is later detected.

A number of methods can be used to generate a variety of functionalities at one or both termini of the target recognition moiety. With the availability of these reactive functionalities so generated, it should be appreciated that a number of chemistries may be used to then link the two components of the probe together. Of the preferred functionalities may be mentioned carboxyl groups, phosphate groups, thiol groups, amino groups, hydroxyl groups and the like. Of the preferred chemical linkages, linking one component to the other, may be mentioned ester linkages, phosphate ester linkages, phosphamide linkages, disulfide linkages, and the like.

One skilled in the art will readily appreciate that the signal generating moiety must also contain an appropriate functionality capable of reacting with the functionality generated at one or both termini of the target recognition moiety. Thus, in some instances, if such a functionality is not already present, an appropriate functionality must also be generated at one or both termini of this signal generating moiety. The following table depicts illustrative functionalities that may be provided at the termini of the target recognition moiety or the signal generating moiety, and the resulting chemical linkage:

| Target Recognition Moiety | Signal Generating Moiety | Chemical Linkage |
| --- | --- | --- |
| 1. phosphate group | hydroxyl group | phosphate ester linkage |
| 2. carboxyl group | hydroxyl group | ester linkage |
| 3. amino group | phosphate group | phosphoamide linkage |
| 4. thiol | sulphydryl | disulfide linkage |

The above-suggested combinations could be completely reversed with respect to the functionalities described for each respective moiety. For example, the target recognition moiety may contain a terminal hydroxyl group while the signal generating moiety contains, or is altered to contain, a phosphate group, and so on.

Referring now to the first illustration in the above table, one or both termini of the target recognition moiety is provided with a phosphate functionality either through chemical means or through enzymatic means. This may be accomplished through the use of well-known phosphorylation techniques in the art such as using polynucleotide kinase and ATP or performing phosphorylation during chemical synthesis, and the like. The signal generating moiety may contain a terminal hydroxyl group. Alternatively, it may be modified by well-known phosphorylation procedures to contain a phosphate group which is then converted to an amine, carboxyl, or thiol group, using conventional chemistry. The two moieties, now containing appropriate terminal reactive functionalities, are then allowed to react using conventional methods such as coupling with water soluble carbodiimides, or the linking of the two components by the use of heterobifunctional reagents.

Figure 1:
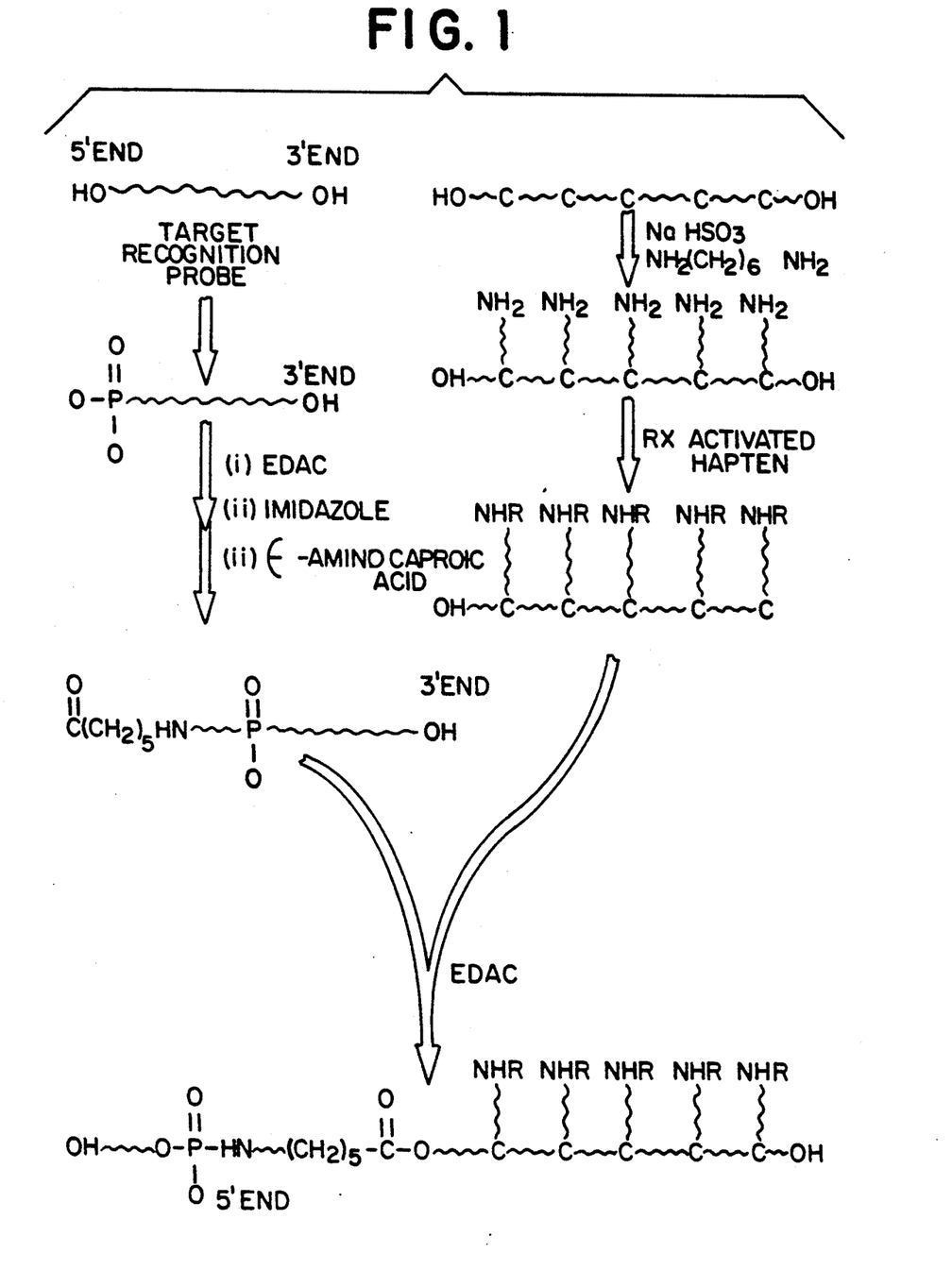
FIG. 1 is a schematic representation of one embodiment of the invention wherein the target recognition moiety is modified to contain at least one terminal carboxyl functionality, and then reacted with signal generating moiety via an ester linkage, to form a nucleotide probe.

Referring now to the second illustrative combination, which reaction scheme is also illustrated by FIG. 1, the target recognition sequence is modified to contain a carboxyl functionality at one or both termini. In a preferred embodiment, this may be accomplished by first phosphorylating either the 3' end or the 5' end. The phosphate group of the phosphorylated DNA is then activated with an imidazole/ethyl-dimethylamino-propyl carbodiimide (EDAC), and then reacted with an excess of an amino acid such as ε-amino caproic acid to reacted with 5' or 3' amino functionalities provided on the target recognition moiety, to form a Schiff's Base followed by borohydride reduction. The following depicts these last-mentioned schemes:

produce the carboxyl group. The target recognition moiety is then reacted with signal generating moiety containing a reactive terminal hydroxyl group in the presence of excess EDAC to form an ester linkage, chemically linking the two moieties.

Figure 2:
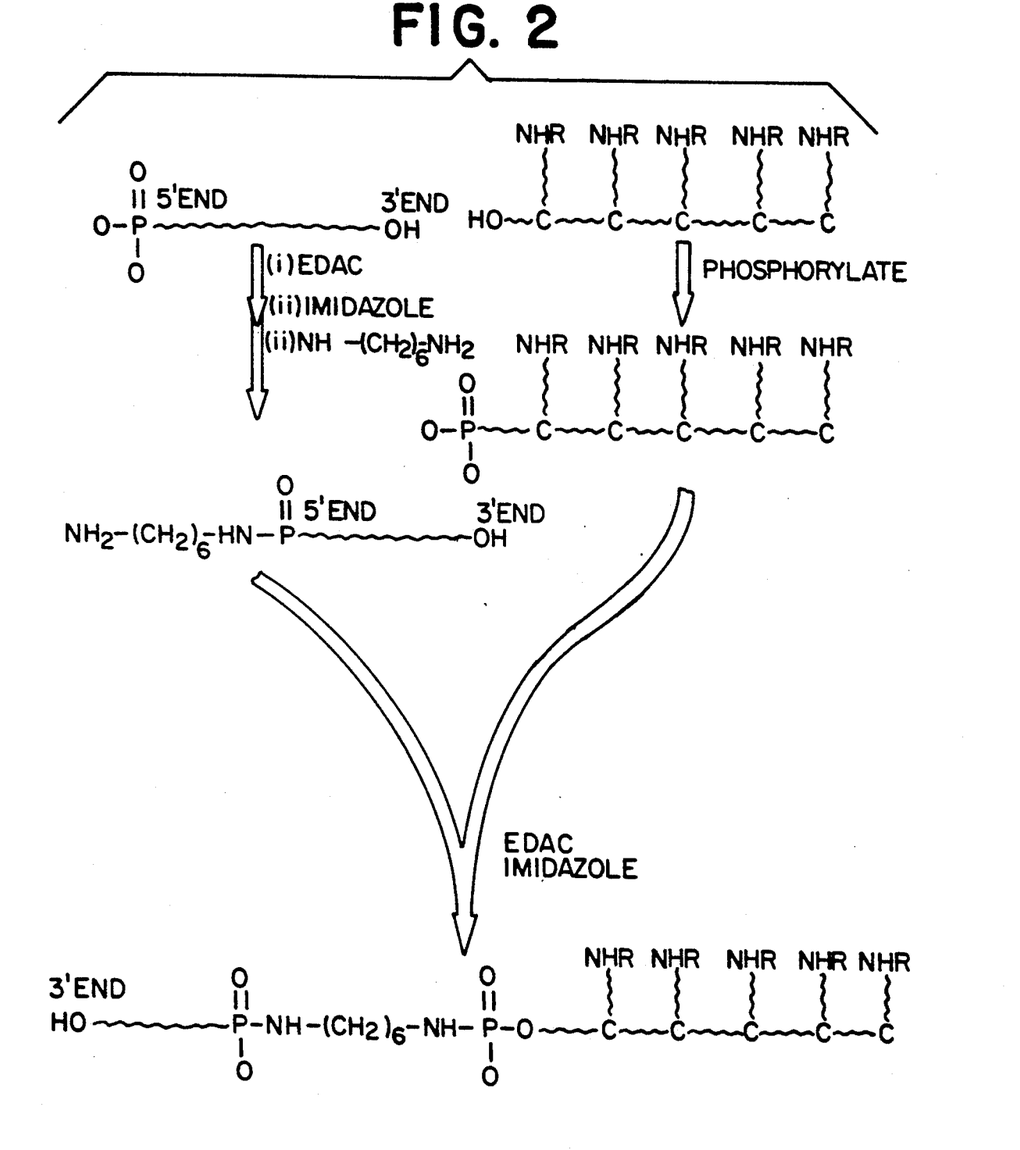
FIG. 2 is a schematic representation of a second embodiment of the method of the invention wherein the target recognition moiety is provided with at least one terminal amino functionality for formation of a phosphoamide linkage with signal generating moiety, to form a nucleotide probe.

Referring now to the third permutation, which reaction sequence is further illustrated by FIG. 2, a phosphorylated target recognition moiety is provided with an amino functionality by reaction of activated phosphate with a diamine. Preferred is reaction with EDAC as described above for the second illustration, and subsequent reaction with an excess of an alkyldiamine such as hexyldiamine.

In the fourth illustrated combination from the above table, a phosphorylated target recognition moiety is first aminated as described above, the amino functionality then being converted to a thiol group by the use of appropriate heterobifunctional reagents, like N-succinimidyl 3-(2-pyridyl dithio) propionate (SPDP). In this combination, one or both termini of the signal generating moiety is provided with a sulphydryl group. The two components are then reacted, using oxidative couplings, to form a disulfide linkage, or by the use of a maleimide group on one end and SH on the other.

As referred to above, the signal generating moiety comprises any polymer capable of containing a detectable label, which polymer is further capable of chemical linkage to one or both termini of the target recognition moiety. Multifunctional polymers may be suitably used to comprise this moiety. For example, polymers may be used which contain carboxyl groups for the labeling portions, such as biotin and the like, and also contain at least one terminal amino functionality for chemical linkage to the target recognition sequence.

Polysaccharides may also be suitably used wherein hydroxyl groups on the terminal monosaccharides are converted to aldehydes which may then react with a target recognition moiety containing a terminal amino functionality.

Ribonucleotides having a diol group at the 3' end may be similarly modified by conventional periodate reaction to yield a dialdehyde. The dialdehyde may then be converted to amino groups by reductive amination and then reacted with target recognition moiety, forming a phosphoamide linkage or any other appropriate linkage. Alternatively, the aldehyde groups may be As alluded to throughout the text, one or both termini of either the signal generating moiety or the target recognition moiety is provided with a reactive functionality as described herein. If both termini of a target recognition moiety are reactive, it is conceivable that a chemical linkage could be formed at both ends with signal generating moiety. The probe would then be constructed with a target recognition moiety flanked on either side with signal generating moiety. If both termini of the signal generating moiety are reactive, the opposite construct would be formed. If each of the components of the nucleotide probe have reactive groups provided at either end, then a repetitive polymer or a cyclic labeled probe could be formed.

In the preferred embodiments, wherein the signal generating moiety comprises nucleotide bases, all possible terminus - terminus combinations are within the contemplation of the invention. For example, the chemical linkage may be a 5' to 5' linkage, a 3' to 3' linkage, or a 5' to 3', or a 3' to 5' linkage. Each prospective terminus would be provided in a suitable manner with the functionality capable of reacting with the terminus of the other component.

The nucleotide probe constructed as above may be provided as a reagent solution, comprising one or more nucleotide probes as described herein, and a buffer. Suitable buffers are generally aqueous and may contain dextran sulfate, EDTA, and similar additives, whether present alone or in any combination, provided that the additives are compatible with the subsequent hybridization of the reagent to target analyte. The reagent solution may also comprise agents that enhance the ability of the probe to bind to target, such as suitable hybridization enhancers, carrier DNA, and compounds to increase the specificity, such as formamide. In this solution format, the shelf-life of the probe reagent generally ranges over a year. Alternatively, the probe may be lyophilized and thus provided in dry reagent form to be reconstituted with buffers such as those described above, prior to the user conducting hybridization assays with sample analyte.

The method and use of the hybridization probe and reagents described by this invention assumes the prior selection of an analyte target polynucleotide sequence. In many embodiments, detection of a particular analyte will be desired because the particular sequence of purine and pyrimidine bases in the target polynucleotide is known or thought to be characteristic of a mutated or normal gene of an organism, and because the presence or absence of this particular mutated or normal gene can be correlated with the presence or absence of an infectious agent, carcinogen, disease state, or some other genetic trait.

The use of the probes as described herein is not limited to any specific method or technique of conducting hybridization to the nucleic acid in a biological specimen, to detect the target sequence. Several hybridization assay techniques are known to the art and include, for example, dot blot hybridization, Southern blotting; sandwich hybridization assays such as those described by Ranki, et al., in U.S. Pat. Nos. 4,563,415 and 4,486,539; sandwich hybridization on beads as described by Hansen, et al. in European Patent Application 84306513.7; displacement hybridization techniques such as those described in WO 87/03911; capture techniques wherein the nucleic acid probes as described herein are first immobilized onto a solid support and then contacted with sample; in situ hybridization such as those cited or described by Ploeg, Folia Histochemica et Cytobiologica, Vol. 24 (1986) No. 3, pp 189-194; and the like.

The target analyte nucleotide sequence may be present in various media, most often in a biological, physiological, or environmental specimen. It is preferred in some cases to subject the specimen containing the target analyte sequence to a variety of extraction, purification, and isolation protocols before conducting analysis according to the methods of this invention. Measures such as these are desirable to rid the sample of substances that might interfere with binding of the analyte to the hybridization probe. Examples of such protocols may be found in the second chapter of *Nucleic Acid Hybridization*, ed. B. Hames & S. Higgins, IRL Press, Washington, D.C. (1985), and in standard textbooks.

It is also within the contemplation of the present invention that synthetic homo- or hetero- polynucleotides can be prepared in the laboratory to serve as the target analyte sequence despite their abiological origins, as such synthetic polynucleotides are often desirable for research purposes and the like.

Notwithstanding the foregoing, it is preferred in some cases that the target analyte sequence be in a single-stranded form to facilitate hybridization to the target recognition moiety of the hybridization probe formed by the methods of the invention. Sample containing target analyte nucleotide sequences must often be treated to convert any target analyte to single-stranded form. This conversion to single-stranded form may be accomplished by a variety of ways conventional to the art. For example, the denaturation of duplex nucleic acids can be accomplished thermally, chemically or in other conventional ways. The denaturation process will depend upon the pH, ionic strength, temperature, and other properties of the ambient medium (e.g., presence of urea, formamide, glyoxal, methyl mercury hydroxide or other agents), as well as upon the base composition (i.e., the GC/AT ratio), sequence, and length of the duplex nucleic acid. Reviews of various methods of denaturation may be found in standard textbooks, and in J. Marmur, C. Schildkraut and P. Dory in *Molecular Basis of Neoplasia*, Univ. of Texas Press, Austin, Tex., 1962.

Exemplary of a hybridization reaction are situations wherein the target analyte sequence is present in a liquid medium. This medium may take many forms, most illustrative of which is unprocessed biological fluid. The unprocessed biological fluid can be mixed with a "second solution" in some embodiments so as to produce a medium known to support rehybridization of complementary single-stranded nucleic acids.

The second solution may be aqueous or nonaqueous or a mixture of both. Certain inorganic or organic additives known to affect rehybridization of complementary single-stranded nucleic acids may be added to enhance the rate of hybridization and/or to increase the equilibrium extent of rehybridization (i.e., stability of the rehybridized form). Of the inorganic additives may be mentioned sodium citrate and sodium chloride; of the organic compounds may be mentioned such compounds as formamide. Other useful additives are polyethylene glycol, dextran sulfate, sodium dodecyl sulfate and casein.

The probe may be contacted with a liquid sample under conditions in which the analyte target sequence, if present, can hybridize in whole or in part to a complementary region contained in the target recognition moiety of the nucleotide probe. This contacting step may be effectuated in a variety of ways, and under varying conditions of "stringency". A review of factors which affect rehybridization (reassociation) processes is available in *Nucleic Acid Hybridization*, ed. B. Hames and S. Higgins, IRL Press, Washington, D.C. (1985). The factors include conditions of temperature, pH, salt concentration and solvent medium, in addition to factors which reflect the length, complexity, and degree of complementarity of the probe and analyte target polynucleotides. The contact period may vary depending on the length of time necessary to effect hybridization to the desired extent, which is dependent in part on the length of the binding region in the target recognition moiety as well as the reaction conditions.

The nucleotide probe, with any bound complementary target analyte sequence, is separated from the biological sample after the desired hybridization has taken place. This separation may be accomplished by any suitable procedure including, but not limited to chromatography (column, gel, etc.), filtration, electrophoresis (including electroelution) and the like. It may be further desirable to incorporate a rinsing step to ensure that unbound material is fully separated from rehybridized material which has bound to the probe.

Once the hybridization event has taken place and the bound material is separated from unbound, detection of the label on the signal generating moiety is undertaken by assaying the bound material, unbound material, or both.

If the label is a radioactive one, direct detection can be accomplished through conventional radioisotopic quantitation techniques.

If the label is a chemical one, as for example, biotin, indirect detection takes place. Examples of this include contact with a chromogenic substrate, or the like, well-known to the art.

The following examples provide more specific embodiments of the present invention, but are not to be considered limitative thereof.

EXAMPLES

Preparation of Oligomers For Use as Signal-Generating and Target Recognition Moieties All oligonucleotides were synthesized by typical phosphoramidite chemistry on a DNA synthesizer using 5 Phosphate-on cyanoethyl phosphoramidite after which the oligomer was deblocked to remove the protecting groups. Alternatively, the phosphate group was added by the action of polynucleotide kinase (after deblocking). The oligomer was purified after the synthesis over a column containing dextran gel beads having an exclusion volume of about 25,000 daltons (SEPHADEX G 25, Pharmacia, Inc., Piscataway, N.J.).

The signal generating moiety oligomer was synthesized on a DNA synthesizer and in some cases the capping step after each coupling was eliminated. This oligomer was 50–200 bases in length; with 20–100% of the bases being cytosines. After deblocking and then desalting over a column containing dextran gel beads having an exclusion volume of about 25,000 daltons (SEPHADEX G 25, Pharmacia, Inc., Piscataway, N.J.), the oligomer was lyophilized and the exocyclic amino groups of the C's were transaminated by adding 2 mls of the transamination mix of the dried oligomer and shaken at room temperature for 24–72 hours. The transamination mix was made up as follows: 5.67 g of the hexanediamine dihydrochloride was mixed with 0.231 g of morpholinoethane sulfonic acid in 500 microliters of concentrated sodium hydroxide in a 50 ml screw capped tube. The volume was brought to 9.5 mls with warm water and the mixture was shaken until it was mostly dissolved. 1 g of the sodium metabisulfite was added and dissolved, and the pH was adjusted to 6.0–6.2. After the reaction proceeded for 24–72 hours, the pH was brought up to 8.5 for two hours, and then reduced for 7 to 30 minutes. The product was then purified over a column containing 1×40 cm dextran gel beads having an exclusion volume of about 50,000 daltons (SEPHADEX G 50, Pharmacia, Inc., Piscataway, N.J.).

Haptenylation of the Signal Generating Oligomer

The transaminated signal generating moiety oligomer was haptenylated with either biotin or fluoroscein isothiocyanate (FITC) either before or after linking to target recognition moiety oligomer. In either case, the biotin (NHS-LC-biotin) or FITC was dissolved in dimethylformamide and mixed with an equal volume of the transaminated oligomer dissolved in 0.1M sodium bicarbonate, pH 9.0, so that the ratio of hapten to amino groups was at least 2. The mixture was allowed to stand at room temperature for 16 hours. Unreacted hapten was removed by chromatography with dextran gel beads having an exclusion volume of about 25,000 daltons (SEPHADEX G 25, Pharmacia, Inc., Piscataway, N.J.). Alternatively, the excess FITC was removed by one or two butanol extractions followed by chromatography with dextran gel beads having an exclusion volume of about 25,000 daltons (SEPHADEX G 25, Pharmacia, Inc., Piscataway, N.J.). In both cases, the purified oligomer was lyophilized and redissolved in water.

Preparation of 5' carboxyl oligonucleotide 5 nanomoles of phosphorylated oligonucleotide were dissolved in an aqueous solution containing tenth molar imidazole and tenth molar EDAC (100 microliter, pH 6.0) and were left 20 to 50 degrees centigrade for 1 to 16 hours. The contents were passed through a gel filtration column and to the oligonucleotide containing fractions an equal volume of four tenth molar amino caproic acid were added. After 1–16 hours the carboxylated oligonucleotide was isolated by gel filtration.

Preparation of 5' amino oligonucleotide

To a ml of solution containing 5' phosphorylated oligonucleotide, sixteen microliters of N-methyl imidazole and one mL one fourth molar diaminohexane along with 4 mg EDAC were added, the pH of the solution was adjusted to about 6. After an overnite reaction 5' amino oligonucleotide was isolated by gel filtration.

Preparation of ester linked probes

To a ml. of aqueous solution containing 5 nanomoles each of 5' hydroxyl oligonucleotide and 5' carboxyl oligonucleotide, 10 mg. of EDAC were added. The solutions were left at room temperature overnite after adjusting the pH to 6. The labeled probe was isolated by chromatography with cross-linked agarose gel beads (SEPHAROSE CL6B, Pharmacia, Inc., Piscataway, N.J.) or beads of dextran gel cross-linked with bisacrylamide having an exclusion volume of about 200,000 daltons (SEPHACRYL S-200, Pharmacia, Inc., Piscataway, N.J.).

Preparation of amide linked probes

To a ml. of aqueous solution containing 5 nanomoles of each 5' amino oligonucleotide and 5' carboxyl oligonucleotide, 10 mg. of EDAC were added. The solutions were left at room temperature overnite after adjusting the pH to 6. The labeled probe was isolated by chromatography with cross-linked agarose gel beads (SEPHAROSE CL6B, Pharmacia, Inc., Piscataway, N.J.) or beads of dextran gel cross-linked with bisacrylamide having an exclusion volume of about 200,000 daltons (SEPHACRYL S-200, Pharmacia, Inc., Piscataway, N.J.).

Preparation of phosphoamide and phosphodiester linked probes

To a mi. of aqueous solution containing 5 nanomoles each of 5' amino or 5' hydroxyl oligonucleotide and 5' phosphate oligonucleotide, 10 mg. of EDAC were added. The solutions were left at room temperature overnite after adjusting the pH to 6. The labeled probe was isolated by chromatography with cross-linked agarose gel beads (SEPHAROSE CL6B, Pharmacia, Inc., Piscataway, N.J.) or beads of dextran gel cross-linked with bisacrylamide having an exclusion volume of about 200,000 daltons (SEPHACRYL S-200, Pharmacia, Inc., Piscataway, N.J.).

Chemical Linkage of the Probe Components Using Heterobifunctional Reagents

A number of heterobifunctional reagents from commercial sources (like Pierce Chemicals) are used to link the two components to form a functional probe. Of these reagents may be mentioned Succinimidyl 4-(maleimidomethyl) cyclohexane-1-carboxylate (SMCC), N-Succinimidyl 3-(2-pyridyl dithio) propionate (SPDP), N-Succinimidyl (4-iodoacetyl) aminobenzoate (SIAB), Succinimidyl 4-(p-maleimidophenyl) butyrate (SMPB), and the like. These reagents are adapted to link the probes by separate reaction of the two components with each other.

Characterization of the Product

The labeled probe was characterized in two ways. The first was by polyacrylamide gel electrophoresis, where an increase in the molecular weight of the product was noted as evidence that the linking of the probe to the label was successful. Secondly, the product was shown to be functional in the assay to detect DNA from *Neisseria gonorrhea*. In this assay, the biotin or FITC was detected where the probe had hybridized to *Neisseria gonorrhea*, indicating that the target recognition oligomer was covalently attached to the signal generating oligomer.

What is claimed is:

1. A labeled nucleotide probe formed according to the chemical synthesis having the following steps:
   a) providing a first target recognition moiety comprising a nucleotide sequence of at least about 15 nucleotide bases, said sequence containing a 5' end and a 3' end;
   b) altering said first target recognition moiety with a phosphate group at said 5' end, said 3' end, or both to form a phosphorylated target recognition moiety.
   c) activating the phosphate group of said phosphorylated target recognition moiety of step b) with imidazole and ethyl-dimethylamino-propyl carbodiimide;
   d) reacting said activated phosphate group of said phosphorylated target recognition moiety of step c) with epsilon-amino caproic acid to provide a carboxyl group at said 5' end or said 3' end of said target recognition moiety, wherein said carboxyl group is formed from the carboxyl group of epsilon-amino caproic acid;
   e) providing a second signal generating moiety comprising a nucleic acid sequence having at least one terminus and a length of from about 50 to about 200 bases, and further having at least one detectable label attached thereto wherein said terminus contains a hydroxyl group that is capable of reacting with said carboxyl group provided on said first target recognition moiety;
   f) chemically reacting said carboxyl group on said first target recognition moiety with said hydroxyl group of said second signal generating moiety to covalently join said first target recognition moiety and said second signal generating moiety thereby producing said labeled nucleotide probe.

2. A probe according to claim 1 wherein said signal generating moiety is labeled with a hapten.

3. A probe according to claim 2 wherein said hapten is biotin.

4. A probe according to claim 2 wherein said hapten is fluorescein.

* * * * *